(12) United States Patent
Rosenberg et al.

(10) Patent No.: US 9,746,478 B2
(45) Date of Patent: Aug. 29, 2017

(54) CHARACTERIZATION OF MICROBIAL DEPOSITION AND IMMUNE RESPONSE AT THE BASEMENT MEMBRANE AND METHODS RELATING THERETO

(76) Inventors: E. William Rosenberg, Memphis, TN (US); Patricia W. Noah, Germantown, TN (US); Robert B. Skinner, Jr., Memphis, TN (US); Timothy D. Mandrell, Memphis, TN (US); Jagat Narula, Philadelphia, PA (US); Charles R. Handorf, Memphis, TN (US)

(*) Notice: Subject to any disclaimer, the term of this patent is extended or adjusted under 35 U.S.C. 154(b) by 1325 days.

(21) Appl. No.: 11/588,192

(22) Filed: Oct. 26, 2006

(65) Prior Publication Data

US 2007/0077206 A1    Apr. 5, 2007

Related U.S. Application Data

(62) Division of application No. 09/789,102, filed on Feb. 20, 2001, now abandoned.

(60) Provisional application No. 60/183,647, filed on Feb. 18, 2000.

(51) Int. Cl.
| | |
|---|---|
| A61K 49/00 | (2006.01) |
| A61K 39/395 | (2006.01) |
| A61K 39/02 | (2006.01) |
| G01N 33/68 | (2006.01) |
| G01N 33/564 | (2006.01) |

(52) U.S. Cl.
CPC ....... *G01N 33/6887* (2013.01); *G01N 33/564* (2013.01); *G01N 33/6881* (2013.01); *G01N 2800/20* (2013.01); *G01N 2800/205* (2013.01)

(58) Field of Classification Search
CPC ... A61K 39/00; A61K 39/0002; A61K 39/092
USPC ...... 424/9.1, 9.2, 130.1, 172.1, 234.1, 244.1
See application file for complete search history.

(56) References Cited

U.S. PATENT DOCUMENTS

| | | | | |
|---|---|---|---|---|
| 4,937,188 | A | 6/1990 | Giese et al. | 435/41 |
| 5,589,328 | A | 12/1996 | Mahant | 435/4 |
| 5,665,539 | A | 9/1997 | Sano et al. | 435/6 |
| 5,731,158 | A | 3/1998 | Bobrow et al. | 435/7.5 |
| 6,083,689 | A | 7/2000 | Martinelli et al. | 435/6 |
| 6,143,575 | A | 11/2000 | Kraus | 436/518 |
| 6,228,363 | B1 * | 5/2001 | Naparstek | 424/185.1 |
| 2001/0007020 | A1 * | 7/2001 | Gerl | 530/388.1 |

FOREIGN PATENT DOCUMENTS

WO    WO98/42737    * 10/1998    ........... C07K 14/00

OTHER PUBLICATIONS

Floege, J. et al. Kidney International, vol. 42, pp. 573-585. 1992.*
Noah et al. *Skin basement membrane zone: a depository for circulating microbial antigen evoking psoriasis and autoimmunity.* SKINmed, vol. 5, (2006), pp. 72-79.

Vassilev et al. *Inhibition of cell adhesion by antibodies to Arg-Gly-Asp (RGD) in normal immunoglobulin for therapeutic use (Intravenous immunoglobulin, IVIg).* Blood, vol. 93, No. 11, (1999), pp. 3624-3631.
Hirabayashi et al., "Port-site metastasis after CO2 pneumoperitoneum: role of adhesion molecules and prevention with antiadhesion molecules" Surg Endosc., 18(7):1113-1117, Jul. 2004.
Shannon et al., "Anti-metastatic properties of RGD-peptidomimetic agents S137 and S247", Clin Exp Metastasis 21(2):129-138, 2004.
Baughn et al. Evidence that autologous idiotypic regulation of anti-arginine-glycine-aspartic acid autoantibodies may influence development and progression of syphilitic lessions in infected rabbits. Infection and Immunity, vol. 60, No. 9, (1992), pp. 3861-3871.
Fearon, Innate immunity and the biological relevance of the acquired immune response. QJM: An International Journal of Medicine, vol. 92, (1999), pp. 235-237.
Freireich et al. Quantitative comparison of toxicity of anticancer agents in mouse, rat, hamster, dog, monkey, and man. Cancer Chemotherapy Reports, vol. 50, No. 4, (1966), pp. 219-244.
Joh et al. Role of fibronectin-binding MSCRAMMs in bacterial adherence and entry into mammalian cells. Matrix Biology, vol. 18, (1999), pp. 211-223.
Kostrzynska et al. Binding of laminin, type IV collagen, and vitronectin by *Streptococcus* pneumoniae. Zentralbl Bakteriol., vol. 277, (1992), pp. 80-83.
Noah et al. Streptococcal products in the epidermis of patients with streptococcal associated psoriasis: detection by immunofluorescence with monoclonal and polyclonal antostreptococcal antibodies. Clinical Research, vol. 34, No. 1, (1986), p. 771A.
Noah, P. The role of microorganisms in psoriasis. Seminars in Dermatology, vol. 9, No. 4, (1990), pp. 269-276.
Skinner et al. Antimicrobial treatment of psoriasis. Dermatologic Clinics, vol. 13, No. 4, (1995), pp. 909-913.
Swerlick et al. Monoclonal antobodies cross-reactive with group a streptococci and normal and psoriatic human skin. The Journal of Investigative Dermatology, vol. 87, (1986), pp. 367-371.
Talanin et al. Detection of streptococcal class I M protein in prosriasis by confocal immunofluorescent microscopy. Acta Dermatolo.
Truyens et al. High circulating levels of fibronectin and antibodies against its RGD adhesion site during Mouse Trypanosoma cruzi infection: relation to survival. Experimental Parasitology, vol. 80, (1995), pp. 499-506.
Vasey et al. Possible involvement of group A streptococci in the pathogenesis of proriatic arthritis. Journal of Rheumatology, vol. 9, No. 5, (1982), pp. 719-722.
Whyte et al. Acute guttate psoriasis and streptococcal infection. Archives of Dermatology, vol. 89, (1964), pp. 350-356.
Trachsel et al. A human mAb specific to oncofetal fibronectin selectively targets chronic skin inflammation in vivo. Journal of Investigative Dermatology, vol. 127, (2007), pp. 881-886.
Braverman, I., "Protective effects of erythema nodosum in coccidioidomycosis," The Lancet, vol. 353, p. 168 (Jan. 16, 1999).

(Continued)

*Primary Examiner* — Rodney P Swartz
(74) *Attorney, Agent, or Firm* — Jenkins, Wilson, Taylor & Hunt, P.A.

(57) ABSTRACT

Methods for diagnosing a systemic or autoimmune disorder and methods for treating the same by inducing the production of or otherwise providing an autoantibody that recognizes a skin basement membrane component.

8 Claims, 4 Drawing Sheets

(56) References Cited

OTHER PUBLICATIONS

Belew-Noah et al., "Microbial Associations and Response to Antimicrobials Seen in a Psoriasis Clinic," Strepococci and the Host, Plenum Press (New York, NY), p. 157-159, (1997).

Belew-Noah et al., "The Psoriasis Band Test: Detection of Microbial Antigen Deposited in the Skin of Psoriasis Patients Using Amplification Staining with Streptavidin-Biotin Alkaline Phosphatase," J. Invest. Med., vol. 41 (No. 1), p. 2A, (1995).

Cronin et al., "Immunologic Evidence for the In Situ Deposistion of Cytoplasmic Strptococcal Antigen (Endostreptosin) on the Glomerular Basement Membrane in Rats," Clin. Nephrol., vol. 34 (No. 4), p. 143-146, (1990).

El-Shoura SM, "Falciparum Malaria in Naturally Infected Human Patients: X. Ultrastruictual Pathological Alterations of Renal Glomeruli," Parasite, vol. 1 (No. 3), p. 205-210, (1994).

Hoang-Xuan et al., "Epidermolysis Bullosa Acquisita Diagnosed by Direct Immunoelectron Microscopy of the Conjunctive," Opthalmology, vol. 104 (No. 9), p. 1414-1420, (1997).

Hoang-Xuan et al., "Pure Ocular Cicatricial Pemphgoid: A Distant IMmunopathologic Subset of Cicatricial Pemphigoid," Opthalmology, vol. 106 (No. 2), p. 355-361, (1999).

International Search Report for corresponding PCT Application No. PCT/US01/05328 dated May 9, 2001.

Noah et al., "Group A *Streptococcus* Exoenzyme Antigen and Candida Albicans Antigen Deposited in Psoriatic Skin as Demonstrated Using the DAKO LSAB Test," J. Invest. Med., vol. 47 (No. 2), p. 131A, (1999).

Noble et al., "Relationship of the Quality and Quantity of Circulating Anti-BSA Antibodies to the Severity of Glonerulonephritis in Rats with Chronic Serum Sickness," Clin. Exp. Immunol., p. 277-282, (1987).

Rosenberg et al., "Mannan Binding Protein in 20 Unselected Consecutive Patients with Psoriasis," J. Invest. Dermatol., vol. 106 (No. 4), p. 683, (1995).

Rosenberg et al., "Microorganisms and Psoriasis," J. Nat. Med. Assoc., vol. 86 (No. 4), p. 305-310, (1994).

* cited by examiner

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Artificially synthesized peptide sequence

<400> SEQUENCE: 1

Lys Tyr Gly Arg Gly Asp Ser
1               5
```

CHARACTERIZATION OF MICROBIAL DEPOSITION AND IMMUNE RESPONSE AT THE BASEMENT MEMBRANE AND METHODS RELATING THERETO

CROSS REFERENCE TO RELATED APPLICATIONS

This application is a divisional of U.S. patent application Ser. No. 09/789,102, filed Feb. 20, 2001, now abandoned, which itself is based on and claims priority to U.S. Provisional Application Ser. No. 60/183,647, filed Feb. 18, 2000, the entire disclosure of each of which is herein incorporated by reference in their entirety.

TECHNICAL FIELD

The present invention pertains to the characterization of microbial deposition and immune response at the basement membrane of the skin and to methods relating to such characterization. In a preferred embodiment, an autoimmune response at the basement membrane in the skin of a subject has been characterized.

| Table of Abbreviations | |
|---|---|
| BMZ | basement membrane zone |
| DAKO LSAB ® | DAKO linked streptavidin biotin amplification and detection kit |
| ELISA | enzyme-linked immunosorbant assay |
| IFN | interferon |
| IL | interleukin |
| IgA | immunoglobulin class A |
| IgG | immunoglobulin class G |
| MHC | major histocompatability complex |
| HLA | human leukocyte antigen |
| SPE | *Streptococcal* pyrogenic exotoxin |
| Vβ | T cell receptor Vβ |

BACKGROUND ART

Psoriasis is a cutaneous inflammatory disorder characterized by epidermal keratinocyte hyperproliferation. Several theories have been proposed regarding the molecular nature and etiology of psoriasis. Factors that have been invoked to cause or promote psoriasis include genetic composition, immune functions, epithelial functions, proliferative and differentiation signals, and/or environmental factors. See Nickoloff et al. (2000) *Exp Dermatol* 9:359-375. The disparate explanations offered by such theories have directed the development of accordingly different therapeutic strategies.

A prevailing view holds that skin disorders such as psoriasis can develop by an initial immune response to a microbial agent that subsequently evolves to a self-perpetuating auto-immune disease. Thus, a current strategy for therapeutic treatment of psoriasis comprises disruption or suppression of the immune response. In particular, drug design approaches are directed at disruption of various aspects of T-cell function, including mechanisms of recruitment, cell-cell interaction, and cytokine production. See Barker (1998) *Hosp Med* 59(7):530-533.

A second view holds that the psoriasis results from erroneous activation of an epithelial defence system. Such an abnormal defence response is characterized by the activity of superantigens and proinflammatory cytokines. This model asserts to explain the predominance of psoriasis in skin and the resemblance of psoriatic skin to bacterial infection and wound healing. In one aspect, genetic factors are implicated in abnormal epithelial responses to infectious and/or physicochemical skin insults.

A related perspective suggests that inappropriate keratinocyte proliferative and differentiation signals comprise the primary disorder of psoriasis. For example, psoriasis may result from misregulation of neutrophils, which are required for epithelial differentiation and keratinization. This developmental defect can occur in the absence of an infectious challenge.

Yet another model proposes that the interaction among epidermal factors (e.g., adhesion molecules), neuropeptides (e.g., nerve growth factor, Substance P), and T lymphocytes plays a causative role in the development of psoriasis.

Each of the afore-mentioned explanations have been accompanied by limited experimental and/or clinical data. Yet a model, and hence a therapy, that encompasses most, if not all, observations related to psoriasis remains undisclosed and unavailable in the art.

What is needed, then, is a comprehensive model of psoriasis, and more generally, of immune disease and skin disease. Such an understanding can improve current diagnostic and therapeutic strategies for treating psoriasis and other disorders. To this end, the inventors of the present invention suggest that psoriasis is an immunologically mediated response of the epidermis to cope with microbial antigens of external or circulating form. Otherwise stated, psoriasis is the result of a continuous and useful response of the skin to the presence of microbial antigen in the skin. This model reconciles several contrasting views summarized above, and, as will be evident from the disclosure herein, presents a novel approach for treating systemic and auto-immune diseases.

Further, the present invention provides methods for facilitating diagnosis of a systemic or autoimmune disorder by detecting an immune product in a biological sample, particularly at a basement membrane of a biological sample. Further provided are methods for treating a systemic disease (including but not limited to a systemic microbial infection or an autoimmune disease) in a subject by inducing the production of or otherwise providing an autoantibody that recognizes a skin basement membrane element.

SUMMARY OF INVENTION

A method of facilitating diagnosis and treatment of a disorder in a subject is disclosed. The method comprises detecting the presence of an immune product in a skin sample from a subject at the basement membrane of the skin sample, whereby diagnosis and treatment of the disorder is facilitated. In one embodiment, the immune product is a microbial product, preferably an antigen. The presence of the immune product can be detected in a skin sample appearing to be normal and uninvolved in the disorder or in a skin sample involved in the disorder. A representative disorder is an unrecognized systemic infection by a pathogen, an autoimmune disease, a disorder associated with immune product deposition at a basement membrane zone (BMZ), or a skin disorder. A representative skin disorder is psoriasis.

In another aspect, the present invention pertains to the use of a sensitive testing system capable of detecting an immune product at the dermo-epidermal junction. Thus, a method for detecting an immune product at the dermo-epidermal junction of a skin sample is disclosed. The method comprises contacting the skin sample with a reagent capable of detecting the material; and detecting a complex formed between the reagent and the material. In one embodiment, the immune product is a microbial product, preferably an antigen.

A method for detecting the presence of an immune product in a tissue sample from a subject suspected to be suffering from an autoimmune disorder is also disclosed. The method comprises contacting a skin sample from the subject with a reagent capable of detecting an immune product, the skin sample comprising a dermo-epidermal junction, a lesional epidermis overlying the dermo-epidermal junction, or both the dermo-epidermal junction and the overlying lesional epidermis; and detecting the presence of an immune product at the dermo-epidermal junction with the reagent. In one embodiment, the immune product is a microbial product, preferably an antigen.

The present invention also discloses a method for detecting the presence of an immune product in a tissue sample from a subject suspected to be suffering from a systemic disorder, the method comprising: (a) contacting a tissue sample from the subject with a reagent capable of detecting an immune product, the tissue sample comprising a basement membrane from kidney; and (b) detecting the presence of an immune product by detecting the presence of material derived from the immune product at the basement membrane from kidney with the reagent. In one embodiment, the immune product is a microbial product, preferably an antigen. The method can be used to detect an immune product associated with a Streptococcal-associated disease, for example, glomerulonephritis.

Further disclosed is a method for detecting the presence of an immune product in a tissue sample from a subject suspected to be suffering from a cardiac disease, the method comprising: (a) contacting a tissue sample from the subject with a reagent capable of detecting an immune product, the tissue sample comprising a basement membrane from heart; and (b) detecting the presence of an immune product by detecting the presence of material derived from the immune product at the basement membrane from heart with the reagent. In one embodiment, the immune product is a microbial product, preferably an antigen. The method can be used to detect an immune product associated with a cardiac disease such as rheumatic fever.

A method of treating a systemic disease in a subject is also disclosed. The method comprises inducing the production of or otherwise providing an antibody against a skin basement membrane element in the subject, whereby treatment of the systemic disease is accomplished. Representative systemic diseases include an infection by a pathogen, an autoimmune disorder, a skin disorder, and a disorder associated with immune product deposition at a BMZ.

A method for treating a proliferative skin disorder is also disclosed. The method comprises detecting the presence of an immune product at the basement membrane of the skin in a subject suffering from a proliferative skin disorder; and inducing the production of or otherwise providing an antibody that recognizes a BMZ component in the subject to thereby treat the proliferative skin disorder. A representative proliferative skin disorder is psoriasis. In one embodiment, the immune product is a microbial product, preferably an antigen.

Accordingly, it is an object of the present invention to provide novel methods pertaining to the characterization of immune product deposition and immune response at the basement membrane. This object is achieved in whole or in part by the present invention.

An object of the invention having been stated hereinabove, other objects will become evident as the description proceeds herein below.

DETAILED DESCRIPTION OF THE INVENTION

I. Definitions

Figure 1:
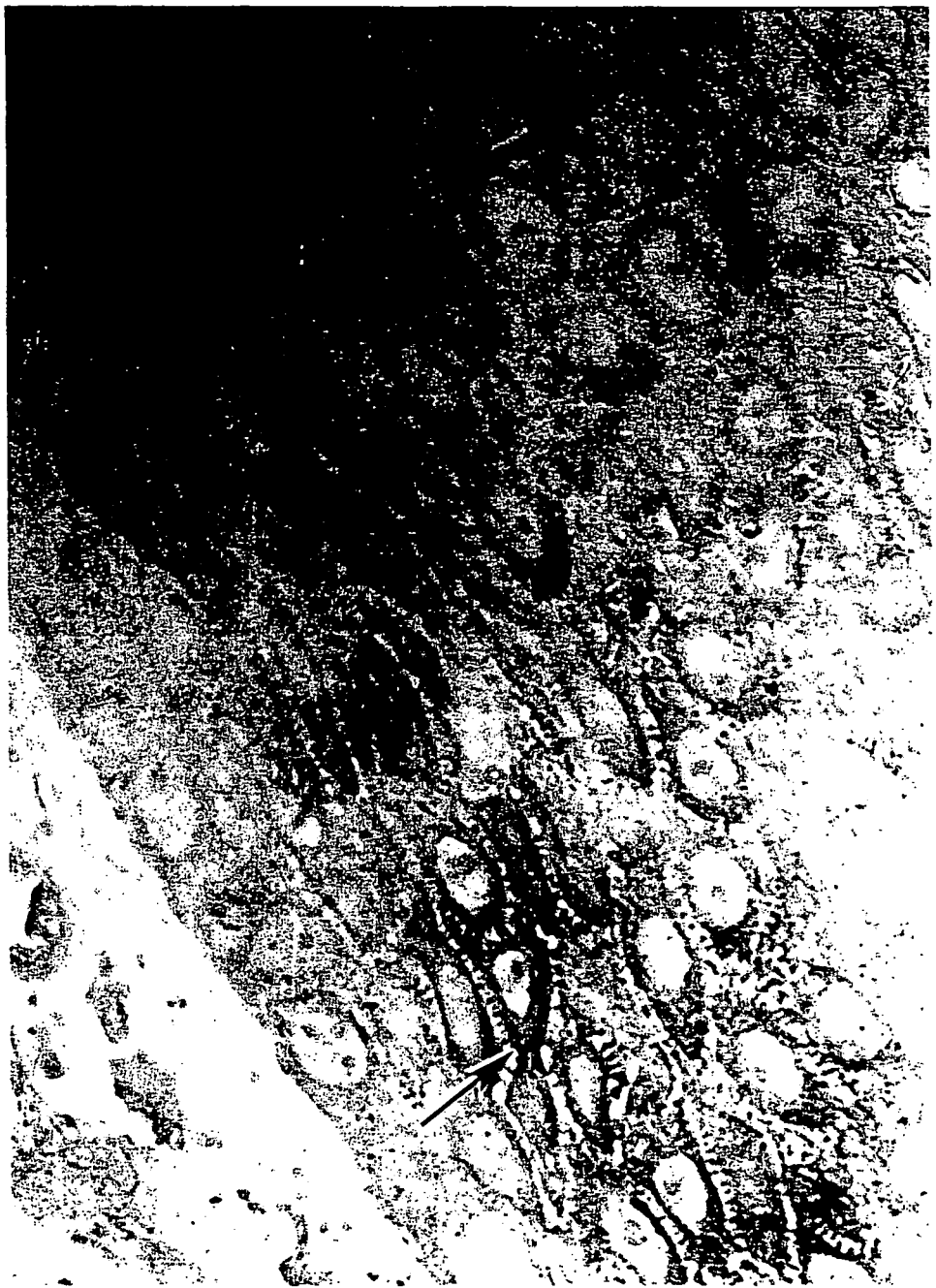
FIG. 1 is a photograph depicting immunohistochemical detection of Streptococcal exoenzymes using an anti-STREPTOZYME® antibody in cells at a lesional psoriatic site (e.g., arrow). According to the procedure used, positive detection of the Streptococcal antigen is observed as a pink or red precipitate (darker areas in photograph). Unstained cells or cellular regions show a substantial lack of pink or red precipitate (lighter areas in photograph). In this view, staining is detected predominantly in the cytoplasm of lesional cells and the nuclei of the same cells are unstained.

While the following terms are believed to be well understood by one of ordinary skill in the art, the following definitions are set forth to facilitate explanation of the invention.

The term "basement membrane zone" or "BMZ" each refer to a lamina present at locations including the dermal-epidermal junction of the skin; the base of all lumen-lining epithelia; underlying epithelia of capillaries and venules; around Schwann cells, adipocytes, skeletal and cardiac muscle cells; and the base of parenchymatous cells of exocrine (pancreas, salivary) glands and endocrine (pituitary, thyroid, adrenal) glands. Thus, a "basement membrane zone" or "BMZ" is present in the skin, heart, kidney and other tissues.

The term "basement membrane zone element" or "basement membrane component", or "basement membrane antigen" as used herein each refer to a protein, a carbohydrate, a lipid, a nucleic acid, or combinations thereof. Representative basement membrane elements useful in accordance with the disclosed method, and which are present in the skin, heart, kidney, and other tissues, include collagen IV, collagen XII, fibronectin, laminin, amyloid P, entactin/nidogen, proteoglycans, glypican, chondroitin sulfate proteoglycans, heparan sulfate proteoglycans, perlecan, epiligrin, kalinin, antigens or immune complexes deposited at the basement membrane, and combinations thereof. See Rohrbach & Timpl (1993) *Molecular and Cellular Aspects of Basement Membranes*, Academic Press Inc., San Diego Calif. A BMZ component can also include an immune complex deposited at a BMZ. Thus, these structures and compounds in the skin, kidney, heart, and other tissues can be stained to detect immune products in affected subjects as compared to control subjects, in accordance with the present invention.

The term "immune product" as used herein refers to an antigen or an immune complex.

The term "antigen" refers to a substance that activates lymphocytes (positively or negatively) by interacting with T or B cell receptors. Positive activation leads to immune responsiveness, and negative activation leads to immune tolerance. The term "self antigen" or "autoantigen" are used interchangeably herein and each refer to an autologous substance that behaves as an antigen. An antigen can comprise a protein, a carbohydrate, a lipid, a nucleic acid, or combinations thereof. An antigen can also comprise an immune complex.

The term "immune complex" as used herein refers to a complex formed by interaction of an antigen with an antibody that specifically recognizes the antigen.

The term "systemic disease" or "systemic disorder" are used interchangeably herein and each refers to a disorder that is relevant to the whole body and is not relevant only to a single tissue or organ. Representative systemic disorders include but are not limited to a systemic infection by a pathogen, an autoimmune disorder, or a disorder associated with deposition of immune complexes at the BMZ.

The term "pathogen" and "infectious agent" are used interchangeably herein and each refers to an organism, such as a bacteria, a virus, a fungi, or a protozoan, that can harmfully invade a host organism. Normal microbial flora are also potential pathogens.

The term "autoimmune disease" refers to any disorder wherein self-reactive antibodies and/or self-reactive T lymphocytes contribute to cellular damage. The term "self-reactive" refers to responsiveness to an autologous component. See Lahita et al., eds (2000) *Textbook of Autoimmune Diseases*, Lippincott, Williams, & Wilkins, Philadelphia, Pa.

Systemic and/or autoimmune diseases that involve skin and are particularly relevant to the therapeutic methods disclosed herein include but are not limited to pemphigus vulgaris, pemphigus foliaceus, epidermolysis bullosa acquisita, bullous pemphigoid, bullous dermatosis, systemic lupus erythematosus, lichen planus, psoriasis, Stevens-Johnson syndrome, dermatitis herpetiformis, discoid lupus erythematosus, herpes gestationis, linear IgA bullous dermatosis, paraneoplastic pemphigus, and skin disorders triggered by deposition of pathogens or immune complexes in the skin. Such skin disorders can also be described as proliferative skin disorders. The methods of the present invention can also be employed for the treatment of any autoimmune disease, including but not limited to Crohn's disease, ulcerative colitis, post-Streptococcal acute glomerulonephritis, polyarteritis nodosa, Grave's disease, myastemia gravis, insulin-resistant diabetes, Hashimoto's thyroiditis, hemolytic anemia, pernicious anemia, Good pasture's syndrome, thromocytopenia purpura, rheumatic fever, rheumatoid arthritis, multiple sclerosis Guillain-Barré syndrome, and ankylosing spondylitis.

The term "subject" as used herein refers to any subject that can be treated in accordance with a method of the present invention. The subject treated in the present invention in its many embodiments is desirably a human subject, although it is to be understood that the principles of the invention indicate that the invention is effective with respect to all vertebrate species, including mammals, which are intended to be included in the term "subject". Moreover, a mammal is understood to include any mammalian species in which treatment or prevention of the noted diseases or disorders is desirable, particularly agricultural and domestic mammalian species. Thus, veterinary applications are provided in accordance with the present invention.

The methods of the present invention are particularly useful in the treatment of warm-blooded vertebrates. Therefore, the invention concerns mammals and birds.

More particularly, contemplated is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine (pigs and hogs), ruminants, horses, poultry, and the like.

II. Microbial Infection in Psoriatic Patients

II.A. Detection of Microbial Antigens

The present invention provides methods for facilitating diagnosis of a disorder by detecting the presence of a microbial product, pathogenic agent or immune complex in a biological sample comprising a BMZ of a subject. Preferably, the subject is a human and is suspected of having a disorder such as an infection by a pathogen or an autoimmune disorder. Optionally, such a disorder is manifested as a skin disorder such as psoriasis. In a preferred embodiment, the method comprises procuring a biological sample comprising a BMZ and detecting a microbial antigen at the BMZ of the biological sample. Preferably, the biological sample is a skin sample. Alternatively, the biological sample is a heart tissue sample or a kidney tissue sample.

The disclosed diagnostic method can be performed using any antibody that recognizes an antigen or immune complex deposited at a BMZ. The term "antibody" indicates an immunoglobulin protein, or functional portion thereof, including a polyclonal antibody, a monoclonal antibody, a chimeric antibody, a single chain antibody, Fab fragments, and an Fab expression library. "Functional portion" refers to the part of the protein that binds a molecule of interest. In a preferred embodiment, an antibody of the invention is a polyclonal antibody. Techniques for preparing and characterizing antibodies are well known in the art (See, e.g., Harlow & Lane (1988) *Antibodies: A Laboratory Manual* Cold Spring Harbor Laboratory Press, Cold Spring Harbor, N.Y.). A monoclonal antibody can also be used in accordance with the present invention and can be readily prepared through use of well-known techniques such as the hybridoma techniques exemplified in U.S. Pat. No. 4,196,265 and the phage-displayed techniques disclosed in U.S. Pat. No. 5,260,203.

The use of a molecular cloning approach to generate antibodies, particularly monoclonal antibodies, and more particularly single chain monoclonal antibodies, are also provided. The production of single chain antibodies has been described in the art. See, e.g., U.S. Pat. No. 5,260,203. For this approach, combinatorial immunoglobulin phagemid libraries are prepared from RNA isolated from the spleen of the immunized animal, and phagemids expressing appropriate antibodies are selected by panning on a tissue of interest. The advantages of this approach over conventional hybridoma techniques are that approximately $10^4$ times as many antibodies can be produced and screened in a single experiment, and that new specificities are generated by heavy (H) and light (L) chain combinations in a single chain, which further increases the chance of finding appropriate antibodies. Thus, an antibody of the present invention, or a "derivative" of an antibody of the present invention, can optimally comprise a single polypeptide chain binding molecule which has binding specificity and affinity substantially similar to the binding specificity and affinity of the light and heavy chain aggregate variable region of an antibody described herein.

The phrase "specifically (or selectively or preferably) binds to an antibody", or "specifically (or selectively or preferably) immunoreactive with", when referring to a protein or peptide, refers to a binding reaction which is determinative of the presence of the protein in a heterogeneous population of proteins and other biological materials. Thus, under designated immunoassay conditions, the specified antibodies bind to a particular protein and do not show significant binding to other proteins present in the sample. Specific binding to an antibody under such conditions can require an antibody that is selected based on its specificity for a particular protein. For example, antibodies raised to a protein having a particular amino acid sequence can be selected to obtain antibodies specifically immunoreactive with that protein and not with unrelated proteins.

In one embodiment of the present invention, an anti-*Candida* antibody (Difco Laboratories of Detroit, Mich.) is used. In a preferred embodiment, the present invention provides polyclonal antibodies that specifically bind one or more Streptococcal antigens and that were prepared as disclosed in Example 2. In preparing the polyclonal antibody, a mixture comprising diverse extracellular antigens was particularly useful in evoking antibodies to Streptococcal antigens that can be found circulating in a subject of deposited in a subject's skin. In a more preferred embodiment, the present invention provides an anti-STREPTOZYME® antibody for use in the diagnostic methods of the present invention.

It will be clear to one skilled in the art that the diagnostic method described herein can employ any suitable antibody that specifically recognizes an antigen that is deposited at a basement membrane. For example, in patients displaying psoriasis and psoriatic arthritis, the serum levels of streptolysin-O, deoxyribonuclease B (DNase-B), and hyaluronidase are elevated (Noah (1990) *Semin Dermatol* 9:269-276), and therefore antibodies that specifically recognize such antigens can be useful for performing the methods disclosed herein. Methods for purifying and for recombinant production of antigens such as bacterial exoenzymes are known in the art as disclosed, for example, in U.S. Pat. Nos. 5,945,278 and 5,731,173, herein incorporated by reference.

The detection methods for the present invention can employ any one of a variety of immunoassay formats used to detect antibodies specifically bound to a particular protein, including but not limited to competitive and non-competitive assay systems using techniques such as radioimmunoassays, ELISA (enzyme linked immunosorbent assay), "sandwich" immunoassays, immunoradiometric assays, immunoferritin techniques, gel diffusion precipitation reactions, immunodiffusion assays, in situ immunoassays (e.g., using colloidal gold, enzyme or radioisotope labels), western blot analysis, precipitation reactions, agglutination assays (e.g., gel agglutination assays, hemagglutination assays), complement fixation assays, biological activity neutralization assays, immunofluorescence assays, protein A assays, and immunoelectrophoresis assays, etc. For a description of representative immunoassay formats and conditions, see Harlow & Lane (1988) *Antibodies: A Laboratory Manual* Cold Spring Harbor Laboratory Press, Cold Spring Harbor, N.Y. and Klein & Hořejší, eds (1997) *Immunology*, $2^{nd}$ Edition, Blackwell Science Ltd, Oxford, United Kingdom. As would be apparent to one of ordinary skill in the art after a review of the disclosure of the present invention presented herein, one can elute or otherwise remove a target antigen from a skin sample or other biological sample as necessary prior to employing any of the foregoing detection techniques.

To detect the primary antibody, additional reagents can be used according to standard methods in the art, for amplification and detection of primary antibody binding to an antigen. A representative amplification/detection system is the DAKO LSAB® alkaline phosphatase kit (DAKO Corporation of Carpinteria, Calif.).

Briefly, the DAKO LSAB® alkaline phosphatase kit utilizes a refined avidin-biotin technique in which a biotinylated secondary antibody reacts with several alkaline phosphatase-conjugated streptavidin molecules. Primary antibodies are labeled by a biotinylated link antibody provided in the kit. The alkaline phosphatase reaction is developed using the New Fuchsin chromogen, also provided in the kit, producing an insoluble fuchsia-colored precipitate at the antigen site.

It should be understood that any amplification and/or detection system that is compatible with detecting a primary antibody can be used. The DAKO LSAB® kit used herein is exemplary, but not a limitation to successful employment of the disclosed methods for diagnosing a systemic infection, an autoimmune disease, a skin disorder, or a disorder associated with immune product deposition at a BMZ. Representative alternative amplification and/or detection systems include a heterogeneous immunoassay using a precipitable solid phase as disclosed in U.S. Pat. No. 6,143,575; chemiluminescence-based assays for detection of enzymes, such as alkaline phosphatase, that catalyze the hydrolysis of indoxyl esters as disclosed in U.S. Pat. No. 5,589,328; a method using complementary enzymatically inactive fragments of an active enzyme and related methods as disclosed in U.S. Pat. No. 4,937,188; an immuno-polymerase chain reaction system as disclosed in U.S. Pat. No. 5,665,539; an analyte-dependent enzyme activation system as disclosed in U.S. Pat. No. 5,731,158; a method using an antibody/replicable DNA template system as disclosed in U.S. Pat. No. 6,083,689; and any combinations thereof. As would be apparent to one of ordinary skill in the art after a review of the disclosure of the present invention presented herein, one can isolate DNA or RNA encoding a target antigen from a suitable biological sample (e.g. whole microorganism) as necessary prior to employing any of the foregoing amplification techniques.

In one embodiment, a microbial antigen can be detected in a tissue sample as described, for example, in Example 3. In an alternative embodiment, the microbial antigen can be detected in a protein sample derived from a biological sample using analogous reagents and methods.

A test kit can be assembled for execution of the reaction as per the invention. The test kit contains all necessary chemicals, such as chromatography material, solvents and eluents, test tubes, detergents, antibodies and chemicals for the detection reaction. Such a test kit can optionally be based on endpoint determination by fluorescence reaction or an enzyme-catalyzed reaction. As would be apparent to one of ordinary skill in the art after a review of the disclosure of the present invention presented herein, one can isolate a fresh tissue sample suspected of comprising a target antigen (e.g. a skin sample or other biological sample) as necessary prior to employing the subject test kit. However, in a preferred embodiment, the present inventive methods and kits can detect (e.g. by immunostaining) a target antigen in a fixed tissue sample that has been stored for a substantial period of time (e.g. for years) in a paraffin block pathology library.

II.B. Correlation of Microbial Presence and Clinical Assessment of Psoriasis

Disclosed herein is the detection of *Streptococcus* and *Candida albicans* in skin tissue. Biopsies were taken from both lesional and normal-looking skin of seven patients whose clinical and laboratory findings suggested an active association with *Candidiasis*, oropharyngeal carriage of *Candida*, active Streptococcal infection, or a Streptococcal carrier state. The term "normal skin" as used herein refers to skin that lacks lesions and has an otherwise asymptomatic appearance. Criteria for selecting such patients are described in Example 1 and are further disclosed in Skinner et al. (1995) *Derm Clinics* 13(4):909-913. Streptococcal and *Candida* antigens were detected in biopsied tissue as described in Example 3. Detection of Streptococcal and Candidal antigens correlated well with clinical assessments as summarized in Table 1.

TABLE 1

Clinical Assessment and Microbial Detection in Skin of Psoriasis Patients

| | Primary Antibody | | Clinical Association | |
|---|---|---|---|---|
| Patient | anti-STREPTOZYME ™ | anti-*Candida* | *Streptococcus* | *Candida* |
| PT lesion | + | − | X | |
| PT non lesion | + | − | | |
| CL lesion | + | − | X | |
| CL non lesion | + | − | | |
| CA lesion | + | + | X | |
| CA nonlesion | +/discontinuous | +/discontinuous | | |
| BD lesion | + | + | X | |
| BD nonlesion | ND | + | | |
| CS lesion | + | − | X | |
| CS non lesion | | | | |
| NS lesion | − | + | | X |
| NS nonlesion | ND | ND | | |
| GB lesion | − | + | | X |
| GB non lesion | − | − | | |

+ indicates presence of STREPTOZYME ® or *Candida* antigen as evidenced by positive staining
+/discontinuous indicates the presence of stained cells interspersed with unstained cells
− indicates absence of STREPTOZYME ® or *Candida* antigen as evidenced by lack of staining
X indicates positive clinical assessment of *Streptococcus* or *Candida* associated disease or carriage
ND = not determined
Abbreviations PT, CL, CA, BD, CS, NS, and GB identify individual patients Two of seven patients displayed clinical features and laboratory results indicative of an association with *Candida* but not with *Streptococcus*. Biopsies from lesional skin of both patients were immunoreactive with an anti-*Candida* antibody but not with the anti-STREPTOZYME® antibody.

Figure 2:
FIG. 2 is a photograph depicting immunohistochemical detection of Streptococcal exoenzymes using an anti-STREPTOZYME® antibody in elongated psoriatic papilla of lesional skin. The most intense staining is observed in epidermal cells and at the dermal-epidermal junction (e.g., thin arrow) that are apposed to blood vessels (e.g., thick arrow). According to the procedure used, positive detection of the Streptococcal antigen is observed as a pink or red precipitate (darker areas in photograph). Unstained cells or cellular regions show a substantial lack of pink or red precipitate (lighter areas in photograph).
Figure 3:
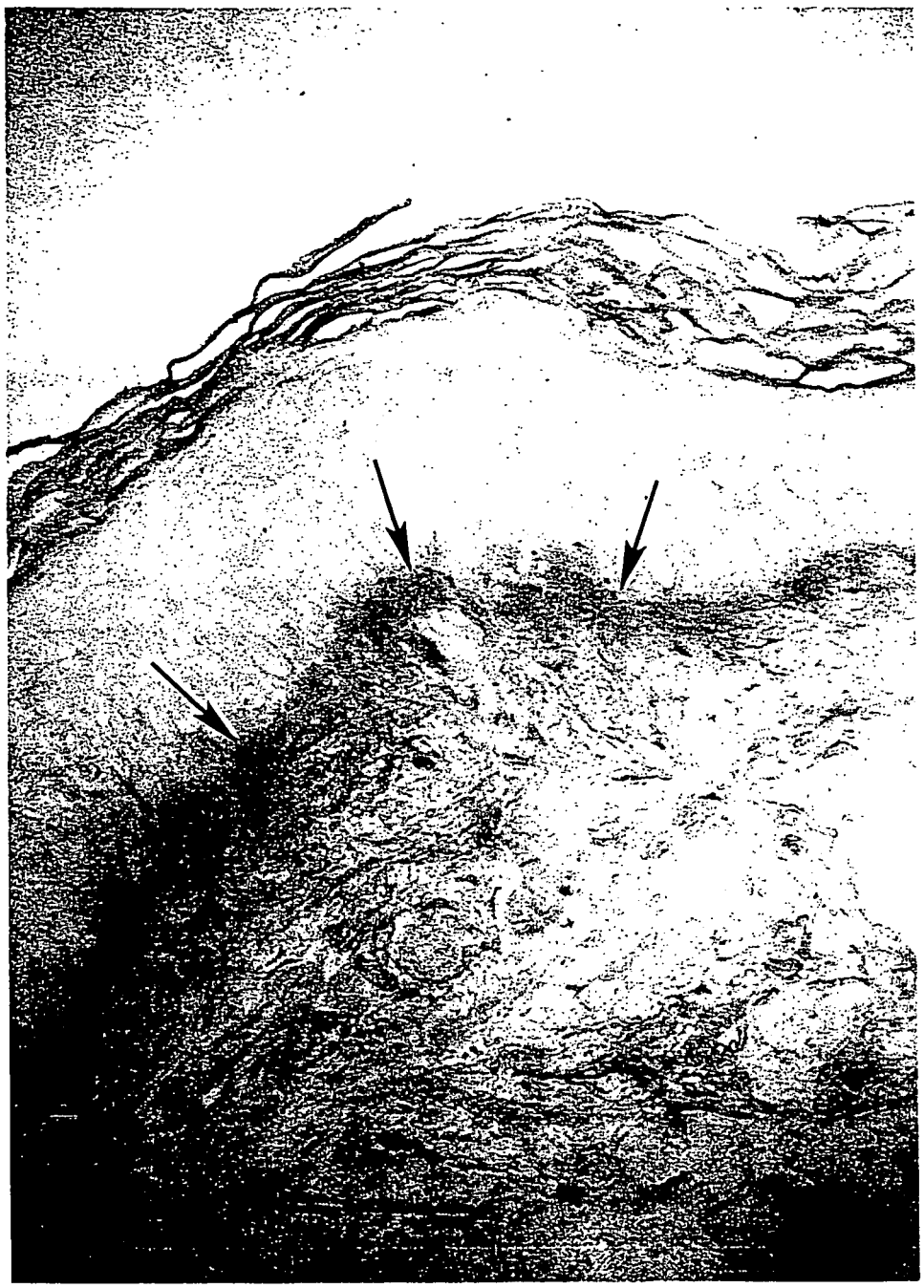
FIG. 3 is a photograph depicting immunohistochemical detection of Streptococcal exoenzymes using an anti-STREPTOZYME® antibody at the basement membrane (arrows) of skin with normal appearance derived from a patient displaying active psoriasis at an alternate site. According to the procedure used, positive detection of the Streptococcal antigen is observed as a pink or red precipitate (darker areas in photograph). Both epidermal and dermal cells appear to lack Streptococcal antigens, observed by the substantial absence of pink or red precipitate in these cells (lighter areas in photograph).
Figure 4:
FIG. 4 is a photograph depicting immunohistochemical detection of Streptococcal enzymes using an anti-STREPTOZYME® antibody in the cytoplasm of epidermal cells of skin with normal appearance derived from a patient displaying active psoriasis at an alternate site. According to the procedure used, positive detection of the Streptococcal antigen is observed as a pink or red precipitate (darker areas in photograph). In this view, epidermal cell nuclei, the basement membrane, and the dermal cell layer are unstained, observed as the absence of a pink or red precipitate therein (lighter areas in photograph).

Five of seven patients displayed clinical features and laboratory results indicative of an association with *Streptococcus*. Using the anti-STREPTOZYME® antibody of the present invention, Streptococcal antigen was detected in both lesional (5 of 5) and non-lesional (2 of 5; 3 of 5 indeterminate staining or not determined as indicated in Table 1) skin of said five patients. Skin biopsies of two of the five patients in this group were also immunoreactive with an anti-*Candida* antibody, although no apparent clinical association with *Candida* was observed. In lesional skin, the STREPTOZYME® antigen was detected in the cytoplasm of epidermal cells at the lesion site (FIGS. 1 and 2), and was particularly concentrated in epidermal cells in apposition to blood vessels (FIG. 2). By contrast, in non-lesional skin of psoriatic patients, the STREPTOZYME® antigen was frequently localized to the epidermal-dermal junction (FIG. 3). In some cases, the STREPTOZYME® antigen was observed in the cytoplasm of epidermal cells, presumably in transit from the basement membrane to the skin surface (FIG. 4).

In these studies, the STREPTOZYME® and *Candida* antigens were not detected in non-lesional skin without also being detected in lesional skin.

The detection of STREPTOZYME® antigen in normal-looking skin of psoriatic patients suggests that examination of random skin biopsies using the disclosed detection method can reveal the systemic presence of suspected microbial material in the absence of skin lesions. Thus, the present invention provides a method for detecting a microbial antigen, whereby a microbial infection is suspected and can then be diagnosed.

III. The Basement Membrane as a Site for Microbial Deposition and Elimination Immune complexes are deposited preferentially in filter sites throughout the body, including the skin, and is mediated by adhesion of immune complexes to BMZ components (e.g., Joh et al. (1999) *Matrix Biol* 18(3):211-223). For example, Streptococcal antigens can bind the basement membrane components laminin and collagen IV (Kostrzynska & Wadstrom (1992) *Zentralbl Bakteriol* 277(1):80-83) and, as disclosed herein, Streptococcal antigens are detected at the dermal-epidermal junction of skin.

While it is not applicants' desire to be bound by any particular theory of operation of the present invention, it is believed that latent autoimmune T cells are activated by recognition of a basement membrane protein to which is bound a microbial antigen. The ability to bind the basement membrane protein/pathogen complex is dependent on innate immunity to pathogenic organisms. An autoimmune reaction ensues as a result of its association with a basement membrane component. In this way, the innate immune reaction facilitates the autoimmune reaction, and the autoimmune activity can increase the efficiency of the immune response to the microbial invader. This mechanism is similar to the proposal that innate immunity collaborates with acquired immunity to create an effective anti-microbial response (Fearon (1999) *Q J Med* 92:235-237).

Thus again, while it is not applicants' desire to be bound by any particular theory of operation of the present invention, it appears that immune product deposition at the BMZ is physiological and useful, and further that autoimmunity at the BMZ (and probably elsewhere) is a physiological, as opposed to a pathophysiological, response. It is thus also envisioned that increasing microbial deposits on the basement membrane concomitantly reduces the burden of disseminated infection on other organs that perform a filtering function. For example, activity in skin to extrude a pathogen can protect kidney from infection by the same pathogen.

The observation, disclosed herein, that STREPTOZYME® antigen accumulates at the basement membrane of non-lesional skin of psoriatic patients demonstrates that the skin basement membrane is an important site where microbial product can be deposited and conveniently eliminated from the circulation. The present invention provides methods for facilitating removal of microbial agents by promoting their localization to a BMZ, described further herein below.

IV. Method of Treating a Systemic Disease

The present invention further provides a method for treating a systemic disease, including but not limited to a pathogenic infection or an autoimmune disease, in a subject by inducing the production of or otherwise providing an antibody against a skin basement membrane element. According to the method, autoantibody production promotes mobility of the virulent or antigenic factor from a vital organ to the skin, whereby it can be subsequently disposed.

The observation was made that immunization of animals with an antigen that elicits autoantibody formation can delay onset and reduce severity of symptoms that are typically elicited in an animal model of syphilis (Baughn & Musher (1992) *Infection and Immunity* 60(9):3861-3871). Among the antibodies that appear in experimental syphilis are those against fibronectin, an important constituent of the skin basement membrane. The 83 kDa receptor protein of *Treponema pallidum* (TpN83) binds to fibronectin at the RGD sequence. To assess the potential of these proteins to contribute to disease progression, animals were immunized with affinity purified (TpN83) or a synthetic peptide (KYGRGDS; SEQ ID NO: 1) that comprises the RGD sequence, and then challenged with *Treponema pallidum*. Accelerated lesion development was observed in animals immunized with the TpN83 antigen. By contrast, animals immunized with the synthetic RGD peptide were markedly resistant to infection. In cases where infection was still manifest, the disease symptoms were substantially attenuated. In a related study, levels of fibronectin and anti-fibronectin autoantibody were found to correlate with recovery from experimental infection of mice with *Trypanosoma cruzi* infection (Truyens et al. (1995) *Exp Parasitol* 90(3): 499-506).

Based on the above-noted observations, Baughn and Musher proposed that the down-regulation or elimination of autoreactive clones is a useful therapeutic approach to impeding disease progression (Baughn & Musher, 1992).

By contrast, the present invention instead provides, in one embodiment, pre-immunization with fibronectin prior to establishment of a disease state as a protective mechanism, whereby the production of autoantibodies is facilitated. The present invention thus provides methods for treating a systemic disease by inducing the production of or otherwise providing an antibody against a basement membrane element (preferably a skin basement membrane element) in the subject. Also provided is a therapeutic composition comprising a substance that can elicit autoantibody production to a basement membrane element or an antibody that specifically recognizes a BMZ component.

The disclosed therapeutic methods are useful for the treatment of any systemic disorder, including but not limited to a systemic infection by a pathogen, an autoimmune disease, a skin disorder, and a disorder associated with deposition of immune products at a BMZ, each described further herein above.

In one embodiment, the disclosed methods can be useful to treat a systemic microbial infection that contributes to the etiology of a psoriatic condition. Representative microbial agents that can comprise an autoantibody-inducing antigen relevant to psoriasis include *Heliobacter pylori, Enterococcus faecalis, Candida albicans*, group A β-hemolytic *Streptococcus*, group B β-hemolytic *Streptococcus*, and *Klebsiella pneumoniae*.

In a preferred embodiment, the production of autoantibodies that recognize these antigens can facilitate elimination of the microbial agent by promoting its movement to the skin, and subsequent disposal. The recovery phase can comprise amelioration of psoriasis and additional symptoms not in skin. For example, treatment of a *Heliobacter pylori* infection according to the disclosed methods can relieve symptoms associated with such an infection, including psoriasis as well as indigestion, heart burn, hernia, reflux, or frank ulcer. Similarly, treatment of an *Enterococcus faecalis* infection according to the disclosed methods can alleviate urinary tract symptoms.

IV.A. Formulation

In accordance with the present invention, BMZ antigens or antibodies that specifically recognize a BMZ component can be formulated into pharmaceutical preparations to be administered to a subject for treatment or prevention of a disorder. A formulation can comprise a combination of a BMZ antigen or an antibody that recognizes a BMZ component with a compatible pharmaceutical carrier and/or adjuvants.

If the BMZ antigen or antibody that recognizes a BMZ component is water-soluble, then it can be formulated in an appropriate buffer, for example, phosphate buffered saline or other physiologically compatible solutions. Alternatively, if the BMZ antigen or antibody that recognizes a BMZ component has poor solubility in aqueous solvents, then it can be formulated with a non-ionic surfactant, such as TWEEN™, or polyethylene glycol. Thus, the compounds and their physiologically acceptable solvents can be formulated for a proposed mode of administration.

Therapeutic formulations of the invention can also include adjuvants or biological response modifiers including, but not limited to, the cytokines IFN-α, IFN-γ, IL-2, IL-4, IL-6, tumor necrosis factor (TNF), or other cytokine affecting immune cells.

For oral administration, the pharmaceutical preparation can be in liquid form, for example, solutions, syrups or suspensions, or can be presented as a drug product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions can take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well-known in the art. Preparations for oral administration can be suitably formulated to give controlled release of the active compound.

For buccal administration, the compositions can take the form of tablets or lozenges formulated in conventional manner. For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, for example, gelatin for use in an inhaler or insufflator can be formulated containing a powder mix of the compound and a suitable powder base such as lactose or starch.

The compositions can be formulated for parenteral administration by injection, e.g., by bolus injection or continuous infusion. Formulations for injection can be presented in unit dosage form, for example, in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic compounds.

The compositions can, if desired, be presented in a pack or dispenser device which can contain one or more unit dosage forms containing the active ingredient. The pack can, for example, comprise metal or plastic foil, such as a blister pack. The pack or dispenser device can be accompanied by instructions for administration.

The invention also provides kits for carrying out the therapeutic regimens of the invention. Such kits comprise in one or more containers therapeutically or prophylactically effective amounts of a modulator and/or a antigenic molecule complex in pharmaceutically acceptable form. The modulator and the antigenic molecule complex in a vial of a kit of the invention can be in the form of a pharmaceutically acceptable solution, e.g., in combination with sterile saline, dextrose solution, or buffered solution, or other pharmaceutically acceptable sterile fluid. Alternatively, the modulator or complex can be lyophilized or desiccated; in this instance, the kit optionally further comprises in a container a pharmaceutically acceptable solution (e.g., saline, dextrose solution, etc.), preferably sterile, to reconstitute the modulator complex to form a solution for injection purposes.

In another embodiment, a kit of the invention further comprises needles or syringes, preferably packaged in sterile form, for injecting the modulator and complex, and/or a packaged alcohol pad. Instructions are optionally included for administration of antigenic molecule complexes by a clinician or by the subject.

IV.B. Dose and Administration of Therapeutic Compositions

The invention provides compositions which enhance the immunocompetence of the host individual. The therapeutic compositions of the present invention have the capacity to prevent the onset and progression of disorders such as systemic infection by a pathogen, an autoimmune disorder, or a disorder associated with deposition of immune complexes at a BMZ. Preferably, the therapeutic composition comprises a BMZ antigen or an antibody that recognizes a BMZ component.

The invention provides methods for determining doses for human immunotherapies disclosed herein by evaluating the optimal dose in experimental animal models and extrapolating the data. Specifically, a scaling factor not exceeding a fifty-fold increase over the effective dose estimated in animals, is used as a preferred prescription method for immunotherapy or vaccination in human subjects.

Conventional methods extrapolate to human dosages based on body weight and surface area. For example, conventional methods of extrapolating human dosage based on body weight can be carried out as using a conversion factor for converting the mouse dosage to human dosage is Dose Human per kg=Dose Mouse per kg×12 (Freireich et al.

(1966) *Cancer Chemotherap Rep* 50:219-244). Doses of therapeutic compositions are also given in milligrams per square meter of body surface area because this measure, rather than body weight, achieves a good correlation to certain metabolic and excretionary functions (Shirkey (1965) *JAMA* 193:443). Moreover, body surface area can be used as a common denominator for drug dosage in adults and children as well as in different animal species as described by Freireich et al. (1966). Briefly, to express a mg/kg dose in any given species as the equivalent mg/sq m dose, multiply the dose by the appropriate km factor. In adult human, 100 mg/kg is equivalent to 100 mg/kg×37 kg/sq m=3700 mg/sq m.

Actual dosage levels of active ingredients in the pharmaceutical compositions of this invention may be varied so as to administer an amount of the active compound(s) that is effective to achieve the desired therapeutic response for a particular subject. The selected dosage level will depend upon the activity of the particular compound, the route of administration, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved. If desired, the effective daily dose can be divided into multiple doses for purposes of administration, e.g., two to four separate doses per day. It will be understood, however, that the specific dose level for any particular subject will depend upon a variety of factors including the body weight, general health, diet, time and route of administration, combination with other drugs, capacity of the subject's system to utilize the active ingredient, the severity of the particular condition being treated, and the degree of the therapeutic effect desired. The selected dosage should be sufficient to produce the desired effect with substantially absent adverse side effects. The dosage can also be adjusted by the individual physician in the event of any complication.

The therapeutic compositions can be administered as a unit dose. The term "unit dose" when used in reference to a therapeutic composition employed in the method of the present invention refers to physically discrete units suitable as unitary dosage for the subject, each unit containing a predetermined quantity of active material calculated to produce the desired therapeutic effect in association with the required diluent; e.g., carrier or vehicle.

The compositions are administered in any manner compatible with the dosage formulation, and in a therapeutically effective amount. The potency of a therapeutic composition can vary, and therefore a "therapeutically effective" amount can vary. However, as disclosed in the Examples, one skilled in the art can readily assess the potency and efficacy of a therapeutic composition of this invention and adjust the therapeutic regimen accordingly. Suitable regimes for administration are also variable, but are typified by an initial administration, optionally followed by subsequent doses. Alternatively, continuous intravenous infusion sufficient to maintain concentrations in the blood in the ranges specified for in vivo therapies can also be employed.

Therapeutic regimens of the present invention can also include adjuvants or biological response modifiers including, but not limited to, the cytokines IFN-α, IFN-γ, IL-2, IL-4, IL-6, tumor necrosis factor (TNF), or other cytokine affecting immune cells.

The mode of administration can include subcutaneous, intramuscular, intravenous or intraperitoneal injection, by inhalation or insufflation (either through the mouth or the nose) or oral, buccal, parenteral, or rectal administration. The number and frequency of therapeutic administration can be modified, depending upon the subject's clinical progress and responsiveness to the immunotherapy.

Representative methods for administering a therapeutic composition comprising an antibody are disclosed in Example 4.

EXAMPLES

The following Examples have been included to illustrate preferred modes of the invention. Certain aspects of the following Examples are described in terms of techniques and procedures found or contemplated by the present inventors to work well in the practice of the invention. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed without departing from the spirit and scope of the invention.

Example 1

Clinical Assessment of Streptococcal or Candidal Infection

Psoriasis patients attending the University of Tennessee Medical Group problem psoriasis clinic, Memphis, Tenn., were chosen after an assessment of the likelihood that their disease was the result of either active Streptococcal or Candidal disease, or carrier states of those microbial products.

Criteria for Streptococcal association included a history of recent flares subsequent to a sore throat, signs of large tonsils, positive cultures of group A beta-hemolytic *Streptococcus* from throat swab, and elevated antibody titers to group A Streptococcal DNase-B, streptolysin O, hyaluronidase, and STREPTOZYME® (Wampole Labs of Cranbury, N.J.). Patients were considered eligible for inclusion if they demonstrated one or more of these findings. Candidal association was assumed in patients found to have characteristic red, scaley plaques on their palms and soles and a positive culture of *Candida albicans* on culture of their oropharynx or dental plates.

Example 2

Generation of Anti-STREPTOZYME® Antibody

A polyclonal rabbit antibody that recognizes Streptococcal exoenzymes was made by injecting STREPTOZYME® reagent (a gift from Dr. Shelby Hall, Wampole Labs of Cranbury, N.J.) emulsified with complete Freund's adjuvant into the foot pad of a New Zealand white rabbit. The rabbit was later injected with an emulsion of STREPTOZYME® reagent and Freund's incomplete adjuvant. The antiserum was collected and aliquotted for storage.

In preparing the polyclonal antibody, a mixture of diverse extracellular Streptococcal antigens was envisioned to be particularly useful in evoking antibodies that recognize *Streptococcus* in a subject's circulation or deposited within a subject's skin. It was reasoned that an antibody raised against a broad spectrum of antigens might demonstrate improved sensitivity in immunoassays when compared to monoclonal antisera directed to Streptococcal M protein of any single serotype, as described by several prior art studies. See Vasey et al. (1982) *J Rheumatol* 9(5):719-722; Whyte et al. (1964) *Arch Dermatol* 89:350; Swerlick et al. (1986) *J Invest Dermatol* 87:367-371; Talanin et al. (1997) *Acta Derm Venerol* 77(3):175-80. Immunoassays using M protein antibodies have not unequivocally demonstrated Streptococcal antigens in psoriatic skin due to cross-reactivity of such antibodies with normal human antigens. Thus, the present invention utilizes an antibody raised against a mixture of Streptococcal antigens, such that the probability of specific detection of Streptococcal antigens is improved.

Example 3

Detection of Microbial Antigens in Skin

Polyclonal anti-STREPTOZYME® was prepared as described in Example 2. Polyclonal rabbit anti-*Candida albicans* was obtained from Difco Laboratories of Detroit, Mich.

Skin biopsy tissue was fixed in formalin according to standard procedures. Primary antibodies were applied to fixed skin tissue and undiluted serum was used. The DAKO LSAB® alkaline phosphatase kit (product No. K682 from DAKO Corporation of Carpinteria, Calif.) was used according to the manufacturer's directions to amplify and detect the primary antibodies.

Skin biopsy tissue stained by this method had been imbedded in paraffin blocks and sectioned. As shown in FIGS. 1-4, tissue sections were analyzed for the presence of immunoreactivity by a pathologist (who had no knowledge of the antisera used) using conventional light microscopy. Detection of the Streptococcal or *Candida* antigen, indicated as "+" in Table 1, was evident as a deep pink-red color resulting from the DAKO LSAB® amplification and detection system used. In a parallel control study, skin tissue from two (2) normal subjects were taken, and these samples lacked a detectable presence of Streptococcal antigen.

Example 4

Generation of Anti-*Trichophyton* Antibody

A polyclonal rabbit antibody that recognizes a *Trichophyton* antigen is made by injecting *Trichophyton* antigen (commercially available in vials from Hollister-Stier Laboratories, LLC of Spokane, Wash.) emulsified with complete Freund's adjuvant into the foot pad of a New Zealand white rabbit. Later, the rabbit is injected with an emulsion of *Trichophyton* antigen and Freund's incomplete adjuvant. The antiserum is collected and aliquotted for storage. The anti-*Trichophyton* antibody from the antiserum is used as a reagent to assay the presence of a fungal antigen in the BMZ of a biological sample, preferably in a skin sample.

Example 5

Animal Model of Treatment of a Systemic Disease

To test the potential protective effect of autoantibodies to skin basement membrane proteins, antibodies that specifically recognize skin basement membrane proteins are administered to a animal model of systemic lupus erythematosus. Ideally, a subject receiving such treatment develops skin rashes as a vital mechanism for disposal of the disease-causing agent.

A model of systemic lupus erythematosus can be generated by any one of a variety of methods, including immunization with proteins or oligopeptides that are lupus autoantigens (Scofield & James (1999) *Semin Arthritis Rheum* 29(3):140-147) and generation of mutant mice that are complement factor B-deficient (Watanabe et al. (2000) *J Immunol* 164(2):786-794). For the purpose of this Example, a mouse model of systemic lupus erythematosus is derived by crossing New Zealand black and New Zealand white mice strains (Stoll and Gavalchin, *Rheumatology* 29:18-27 (2000); Wither & Vukusic (2000) *Immunology* 99(3):345-351).

Antibodies for administration to an animal model of systemic lupus erythematosus specifically recognize a BMZ component and are prepared according to methods well-known in the art. Antibodies can be administered and the progression of psoriasis in response to immunotherapy can be monitored using skills known to one of skill in the art (e.g., Morel et al. (1992) *J Autoimmunity* 5:465-477).

REFERENCES

The references listed below as well as all references cited in the specification are incorporated herein by reference to the extent that they supplement, explain, provide a background for or teach methodology, techniques and/or compositions employed herein.

Assman et al. (2000) *Immunopharm* 47(2-3):203-213.
Baker et al. (1984) *Br J Dermatol* 110:555-564.
Baker (1992) *Br J Dermatol* 126:1-9.
Barker (1994) *Baillieres Clinical Rheumatology* 8:429-438.
Barker (1998) *Hosp Med* 59(7):530-533.
Baughn & Musher (1992) *Infection and Immunity* 60(9): 3861-3871.
Chan et al. (1997) *J invest Dermatol* 110(2):103-109.
Cox (1969) *J Invest Dermatol* 53:428-435.
Eedy et al. (1990) *Br Med J* 300:908.
Ellis et al. (1991) *N Eng J Med* 324:277-284.
Fakler (1994) *Hum Immunol* 40(4):299-302.
Fearon (1999) *Q J Med* 92:235-237.
Freireich et al. (1966) *Cancer Chemotherap Rep* 50:219-244).
Gardembas et al. (1990) *Arch Dermatol* 126:1523.
Glinski et al. (1990) *Arch Derm Res* 282:506-511.
Gottlieb et al. (1995) *Nature Med* 1:442-447.
Griffiths et al. (1986) *Br Med J* 293:731-2.
Grooves et al. (1991) *Br J Dermatol* 124:117-123.
Hall et al. (1981) *J Invest Dermatol* 76:302-303.
Harlow & Lane (1988) *Antibodies: A Laboratory Manual* Cold Spring Harbor Laboratory Press, Cold Spring Harbor, N.Y.
Jee et al. (1998) *Br J Dermatol* 139(6):978-983.
Joh et al. (1999) *Matrix Biol* 18(3):211-223.
Juhlin & Shelley (1977) *Br J Dermatol* 96 (6):577-586.
Kirtschig et al. (1996) *Br J Dermatol* 135:738-745.
Klein & Hořejší, eds (1997) *Immunology*, $2^{nd}$ Edition, Blackwell Science Ltd, Oxford, United Kingdom.
Kostrzynska & Wadstrom (1992) *Zentralbl Bakteriol* 277 (1):80-83.
Lahita et al., eds (2000) *Textbook of Autoimmune Diseases*, Lippincott, Williams, & Wilkins, Philadelphia, Pa.
Leung et al. (1995) *J Clin Invest* 96:2106-2112.
Manjula et al. (1985) *Proc Natl Acad Sci* 82:1064-1068.
Morel et al. (1992) *J Autoimmunity* 5:465-477.
Nickoloff et al. (2000) *Exp Dermatol* 9:359-375.
Noah (1990) *Semin Dermatol* 9:269-276.
Noah et al. (1986) *Clin Res* 34(1):771A.

Narula et al. (1999) *Pub American Registry of Pathology, Armed Forces Institute of Pathology*, Washington, D.C., ISBN 1-881041-47-6.
Oldstone (1987) *Cell* 50:819.
Peters et al. (2000) *Am J Health Syst Pharm* 57(7):645-659.
Prinz et al. (1994) *Eur J Immunol* 24:593-598.
Rohrbach & Timpl (1993) *Molecular and Cellular Aspects of Basement Membranes*, Academic Press Inc., San Diego Calif.
Schmitt-Egenolf et al. (1996) 106(4)711-714.
Schmitt-Egenolf et al. (1994) *J Invest Dermatol* 100(6):749-752.
Scofield & James (1999) *Semin Arthritis Rheum* 29(3):140-147.
Shirkey (1965) *JAMA* 193:443.
Skinner et al. (1995) *Derm Clinics* 13(4):909-913.
Skov and Baadsgaard (2000) *Clin Exp Derm* 25:57-61.
Stoll and Gavalchin (2000) *Rheumatology* 29:18-27.
Swerlick et al., *J. Invest. Dermatol.* 87:367-371 (1986).
Talanin et al. (1997) *Acta Derm Venero.* 77(3):175-80.
Tefler (1992) *Arch Dermatol* 128:39-42.
Trembath et al. (1997) *Human Mol Genet* 6(5):813-820.
Truyens et al. (1995) *Exp Parasitol* 90(3):499-506.
U.S. Pat. No. 4,196,265
U.S. Pat. No. 4,937,188
U.S. Pat. No. 5,260,203
U.S. Pat. No. 5,665,539
U.S. Pat. No. 5,589,328
U.S. Pat. No. 5,731,158
U.S. Pat. No. 5,731,173
U.S. Pat. No. 5,945,278
U.S. Pat. No. 6,083,689
U.S. Pat. No. 6,143,575
Valdimarsson (1993) in *Clinical Aspects of Immunology*, Lachmann et al., eds, pp. 1881-1897, Blackwell Science Ltd, Oxford, United Kingdom.
Valdimarsson et al. (1995) *Immunol Today* 16:145-149.
Vasey et al. (1982) *J. Rheumatol.* 9(5):719-722.
Watanabe et al. (2000) *J Immunol* 164(2):786-794.
Whyte et al. (1964) *Arch Dermatol* 89:350.
Wither & Vukusic (2000) *Immunology* 99(3):345-351.

It will be understood that various details of the invention may be changed without departing from the scope of the invention. Furthermore, the foregoing description is for the purpose of illustration only, and not for the purpose of limitation—the invention being defined by the claims appended hereto.

What is claimed is:

1. A method of treating a disease associated with deposition of immune complexes at a basement membrane zone (BMZ) in a subject, the method comprising inducing the production of an antibody against a skin basement membrane element in the subject, wherein inducing the production of an antibody against a skin basement membrane element comprises administering to the subject a skin basement membrane element, whereby treatment of the disease is accomplished, wherein the disease comprises psoriasis resulting from Streptococcal or Candidal association.

2. The method of claim 1, wherein the skin basement membrane element is selected from the group consisting of collagen IV, collagen XII, fibronectin, laminin, amyloid P, entactin/nidogen, proteoglycans, glypican, chondroitin sulfate proteoglycans, heparan sulfate proteoglycans, perlecan, epiligrin, kalinin, antigens or immune complexes deposited at the basement membrane, and combinations thereof.

3. The method of claim 1, further comprising administering to the subject an antibody against a skin basement membrane element in the subject.

4. A method of treating a disease associated with deposition of immune complexes at a basement membrane zone (BMZ) in a subject, the method comprising administering to the subject an antibody against a skin basement membrane element in the subject, whereby treatment of the disease is accomplished.

5. The method of claim 4, wherein the skin basement membrane element is selected from the group consisting of collagen IV, collagen XII, fibronectin, laminin, amyloid P, entactin/nidogen, proteoglycans, glypican, chondroitin sulfate proteoglycans, heparan sulfate proteoglycans, perlecan, epiligrin, kalinin, antigens or immune complexes deposited at the basement membrane, and combinations thereof.

6. The method of claim 4, wherein the disease comprises psoriasis resulting from Streptococcal or Candidal association.

7. The method of claim 1, wherein the disease comprises a systemic infection by a pathogen, wherein the systemic infection by pathogen comprises a systemic microbial infection.

8. The method of claim 4, wherein the disease comprises a systemic infection by a pathogen, wherein the systemic infection by pathogen comprises a systemic microbial infection.

* * * * *